(12) United States Patent
Saio et al.

(10) Patent No.: US 9,090,782 B2
(45) Date of Patent: Jul. 28, 2015

(54) LIQUID CHEMICAL FOR FORMING WATER REPELLENT PROTECTIVE FILM

(75) Inventors: Takashi Saio, Suzuka (JP); Soichi Kumon, Matsusaka (JP); Masanori Saito, Matsusaka (JP); Shinobu Arata, Matsusaka (JP); Hidehisa Nanai, Tokyo (JP)

(73) Assignee: Central Glass Company, Limited, Ube-shi (JP)

( * ) Notice: Subject to any disclaimer, the term of this patent is extended or adjusted under 35 U.S.C. 154(b) by 118 days.

(21) Appl. No.: 13/703,593

(22) PCT Filed: Jun. 15, 2011

(86) PCT No.: PCT/JP2011/063634
§ 371 (c)(1),
(2), (4) Date: Dec. 11, 2012

(87) PCT Pub. No.: WO2012/002145
PCT Pub. Date: Jan. 5, 2012

(65) Prior Publication Data
US 2013/0092191 A1    Apr. 18, 2013

(30) Foreign Application Priority Data

Jun. 30, 2010 (JP) ................................ 2010-149596
May 13, 2011 (JP) ................................ 2011-108323

(51) Int. Cl.
*C09D 7/12* (2006.01)
*H01L 21/02* (2006.01)
(Continued)

(52) U.S. Cl.
CPC ............... *C09D 7/1233* (2013.01); *C07F 7/10* (2013.01); *C07F 7/12* (2013.01); *H01L 21/0206* (2013.01); *H01L 21/02057* (2013.01); *H01L 21/306* (2013.01); *H01L 21/3105* (2013.01)

(58) Field of Classification Search
None
See application file for complete search history.

(56) References Cited

U.S. PATENT DOCUMENTS 7,838,425 B2    11/2010   Tomita et al.
7,985,683 B2    7/2011    Tomita et al.
(Continued)

FOREIGN PATENT DOCUMENTS

JP    5-299336 A    11/1993
JP    8-164517 A    6/1996
(Continued)

OTHER PUBLICATIONS

Japanese-language Written Opinion dated Aug. 23, 2011 (PCT/ISA/237) (three (3) pages).
(Continued)

*Primary Examiner* — Nicole Blan
(74) *Attorney, Agent, or Firm* — Crowell & Moring LLP

(57) ABSTRACT

The present invention relates to a method for cleaning wafers while preventing pattern collapse of the wafers in semiconductor device fabrication, the wafer having at its surface an uneven pattern and containing silicon element at least on surfaces of recessed portions. Provided is: a liquid chemical for forming a protective film which allows efficient cleaning; and a method for cleaning wafers, using the liquid chemical. A liquid chemical for forming a water repellent protective film is provided for forming a protective film on a wafer (having at its surface an uneven pattern and containing silicon element at least at a part of the uneven pattern), the protective film being formed at least on surfaces of recessed portions of the uneven pattern at the time of cleaning the wafer. The liquid chemical contains a dialkylsilyl compound represented by the formula [1] and does not contain an acid and a base.

$$R_2(H)SiX \quad [1]$$

5 Claims, 2 Drawing Sheets

(51) Int. Cl.
*H01L 21/306* (2006.01)
*H01L 21/3105* (2006.01)
*C07F 7/10* (2006.01)
*C07F 7/12* (2006.01)

(56) References Cited

U.S. PATENT DOCUMENTS

| | | | |
|---|---|---|---|
| 2002/0172895 A1* | 11/2002 | Breen et al. | 430/322 |
| 2008/0241489 A1 | 10/2008 | Ishibashi et al. | |
| 2008/0246036 A1 | 10/2008 | Yamazaki et al. | |
| 2009/0001046 A1* | 1/2009 | Kubota et al. | 216/13 |
| 2009/0305480 A1* | 12/2009 | Sasahara et al. | 438/422 |
| 2009/0311874 A1* | 12/2009 | Tomita et al. | 438/759 |
| 2010/0075504 A1* | 3/2010 | Tomita et al. | 438/706 |

FOREIGN PATENT DOCUMENTS

| | | |
|---|---|---|
| JP | 2005-244203 A | 9/2005 |
| JP | 2008-198958 A | 8/2008 |
| JP | 2008-277748 A | 11/2008 |
| JP | 2010-114414 A | 5/2010 |
| JP | 2010-129932 A | 6/2010 |
| JP | 2011-91952 A | 5/2011 |
| JP | 2012-33873 A | 2/2012 |
| KR | 10-2007-0012352 A | 1/2007 |
| KR | 10-2008-0089296 A | 10/2008 |
| KR | 10-2009-0130828 A | 12/2009 |

OTHER PUBLICATIONS

"Geometrical Product Specification (GPS)—Surface Texture: Profile Method—Terms, Definitions and Surface Texture Parameters", Japanese Industrial Standard JIS B 0601, 2003 (sixteen (16) pages).
Japanese Office Action dated Jul. 10, 2014 (three pages).
Taiwanese Office Action dated Jul. 22, 2014 (five pages).
Corresponding International Search Report with English Translation dated Aug. 23, 2011 (five (5) pages).
Japanese—language Written Opinion dated Aug. 23, 2011 (PCT/ISA/237) (three (3) pages).
"Testing Method of Wettability of Glass Substrate", Japanese Industrial Standard JIS R 3257, 1999 (eighteen (18) pages).
"Geometrical Product Specification (GPS)—Surface Texture: Profile Method-Terms, Definitions and Surface Texture Parameters", Japanese Industrial Standard JIS B 0601, 2003 (sixteen (16) pages).

* cited by examiner

LIQUID CHEMICAL FOR FORMING WATER REPELLENT PROTECTIVE FILM

TECHNICAL FIELD

The present invention relates to a technique of cleaning a wafer in semiconductor device fabrication or the like which technique aims to improve the production yield of devices having a circuit pattern which is particularly fine and particularly high in aspect ratio. More specifically, the present invention relates to a liquid chemical for forming a protective film which liquid chemical aims to prevent a wafer having at its surface an uneven pattern from encountering a pattern collapse.

BACKGROUND OF THE INVENTION

Semiconductor devices for use in networks or digital household electric appliances are being further desired to be sophisticated, multifunctional, and low in power consumption. Accordingly, the trend toward micro-patterning for circuits has been developed, with which micro-sizing of particles has advanced to cause reduction of the production yield. As a result of this, a cleaning step which aims to remove contaminants such as the micro-sized particles and the like is frequently used. As a result, 30-40% of the whole of the semiconductor fabrication process is occupied with the cleaning step.

On the other hand, in cleaning conventionally performed by using a mixed ammonia cleaning agent, damages to the wafer due to its basicity are getting serious with the trend toward micro-patterning for circuits. Therefore, alternation with a dilute hydrofluoric acid-based cleaning agent is taking place.

With this, problems about the damages to the wafer due to cleaning have been solved; however, problems due to an aspect ratio increased with the trend toward micro-processing in the semiconductor devices have become obvious. In other words, a phenomenon where the pattern is collapsed when a gas-liquid interface passes through the pattern is brought about after cleaning or rinsing so as to largely reduce the yield, which has become a significant problem.

The pattern collapse occurs at the time of drawing the wafer out of a cleaning liquid or a rinsing liquid. It is said that the reason thereof is that a difference in height of residual liquid between a part of high aspect ratio and a part of low aspect ratio causes a difference in capillary force which acts on the pattern.

Accordingly, it is expected, by decreasing the capillary force, that the difference in capillary force due to the difference in height of residual liquid is reduced thereby resolving the pattern collapse. The magnitude of the capillary force is the absolute value of P obtained by the equation as represented below. It is expected from this equation that the capillary force can be reduced by decreasing $\gamma$ or $\cos \theta$.

$$P = 2 \times \gamma \times \cos \theta / S$$

(In the equation, "$\gamma$" represents the surface tension of a liquid retained on recessed portions. "$\theta$" represents the contact angle of the liquid retained on the recessed portions to the surfaces of the recessed portions. "S" represents the pattern width of the recessed portions).

In Patent Publication 1, a technique of changing a cleaning liquid from water to 2-propanol before the gas-liquid interface passes through the pattern is disclosed as a method of decreasing $\gamma$ to suppress the pattern collapse.

Additionally, in Patent Publication 2, a technique directed to a resist pattern is disclosed as a method for decreasing $\cos \theta$ in order to suppress the pattern collapse. This method is a method of setting a contact angle to around 90° to bring $\cos \theta$ close to 0 so as to reduce the capillary force to the limit thereby suppressing the pattern collapse.

Additionally, in Patent Publication 3, there is disclosed a cleaning method including: surface-reforming an unevenly patterned wafer surface with a silicon-containing film, by oxidation and the like; forming a water repellent protective film on the surface by using a water-soluble surfactant or a silane coupling agent; reducing the capillary force; and thereby preventing the pattern collapse.

REFERENCES ABOUT PRIOR ART

Patent Publication

Patent Publication 1: Japanese Patent Application Publication No. 2008-198958
Patent Publication 2: Japanese Patent Application Publication No. 5-299336
Patent Publication 3: Japanese Patent No. 4403202

SUMMARY OF THE INVENTION

Problems to be Solved by the Invention

In Patent Publication 3, hexamethyldisilazane and tetramethylsilyldiethylamine are disclosed as a silane coupling agent that forms a water repellent protective film. An object of the present invention is to provide a liquid chemical for forming a protective film on a wafer (formed having at its surface an uneven pattern and containing silicon element at least at surfaces of recessed portions of the uneven pattern) at the time of cleaning the wafer, the liquid chemical containing a silicon compound which serves as an agent that allows forming a protective film with which a water repellency good for preventing the pattern collapse can be exhibited.

Means for Solving the Problems

The present inventors eagerly made studies in order to solve the above-mentioned problems and resulted in using a liquid chemical for forming a protective film which liquid chemical contains a silicon compound having a bond to one hydrogen element as represented by the general formula [1] (the silicon compound will hereinafter be discussed as "a dialkylsilyl compound" in the main body of this specification), as an agent for forming a water repellent protective film capable of reducing the capillary force that acts on the pattern (the agent will hereinafter be discussed as "a water repellent protective film-forming agent" or "a protective film-forming agent"), in order to prevent the collapse of the pattern (hereinafter referred to as "a pattern collapse" in the main body of this specification).

$$R_2(H)SiX \qquad [1]$$

[In the formula, R mutually independently represents at least one group selected from monovalent organic groups having a $C_1$-$C_{18}$ hydrocarbon group and monovalent organic groups having a $C_1$-$C_8$ fluoroalkyl chain. X represents a group selected from halogen groups and monovalent organic groups of which element to be bonded to a silicon element is nitrogen.]

The thus formed protective film was found to provide a greater water repellency as compared with a case where a protective film was formed by using a trialkylsilyl compound such as hexamethyldisilazane and the like (see Example 3 vs. Comparative Example 1, and Example 6 vs. Comparative Example 2). The present inventors also found it possible to form a protective film excellent in water repellency by using a liquid chemical that contained a silicon compound having a certain structure; and an acid or a base serving as a catalyst, and have already filed it as a patent application No. 2011-091952; however, they also obtained a finding that by using a dialkylsilyl compound of the present invention it became possible to obtain a protective film providing an excellent water repellency without the coexistence of acid or base serving as a catalyst (see Examples 1 to 6).

More specifically, the present invention provides inventions as will be discussed in the following [Invention 1] to [Invention 5].

[Invention 1]

A liquid chemical for forming a water repellent protective film, the liquid chemical being able to form a protective film on a wafer that has at its surface an uneven pattern and contains silicon element at least at a part of the uneven pattern, the protective film being formed at least on surfaces of recessed portions of the uneven pattern at the time of cleaning the wafer, comprising:

a dialkylsilyl compound represented by the following general formula [1], wherein an acid and a base are not contained.

$R_2(H)SiX$         [1]

(In the formula, R mutually independently represents at least one group selected from monovalent organic groups having a $C_1$-$C_{18}$ hydrocarbon group and monovalent organic groups having a $C_1$-$C_8$ fluoroalkyl chain. X represents a group selected from halogen groups and monovalent organic groups of which element to be bonded to a silicon element is nitrogen.)

[Invention 2]

A liquid chemical for forming a water repellent protective film, as discussed in Invention 1, wherein X represented in the general formula [1] is a halogen group.

[Invention 3]

A liquid chemical for forming a water repellent protective film, as discussed in Invention 1, wherein X represented in the general formula [1] is a monovalent organic group of which element to be bonded to a silicon element is nitrogen.

[Invention 4]

A liquid chemical for forming a water repellent protective film, as discussed in Invention 1, wherein the dialkylsilyl compound represented by the general formula [1] is represented by the following general formula [2].

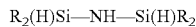

$R_2(H)Si-NH-Si(H)R_2$         [2]

(In the formula, R is identical to that in the general formula [1].)

[Invention 5]

A method for cleaning a wafer that has an uneven pattern at its surface and contains silicon element at least at surfaces of recessed portions of the uneven pattern, comprising:

a cleaning step with a water-based cleaning liquid, in which a surface of the wafer is cleaned with a water-based cleaning liquid;

a water repellent protective film-forming step, in which a liquid chemical for forming a water repellent protective film is retained at least in the recessed portions of the wafer so as to form a water repellent protective film on the surfaces of the recessed portions;

a liquid removal step for removing a liquid from the surface of the wafer; and a water repellent protective film-removing step for removing the water repellent protective film from the surfaces of the recessed portions, wherein the liquid chemical for forming a water repellent protective film, as discussed in any of Inventions 1 to 4 is used in the water repellent protective film-forming step:

In Patent Publication 3, a hydroxyl group formed on the unevenly patterned surface is bonded to a trialkylsilyl group thereby forming a water repellent protective film. From the fact that hydrocarbon groups have hydrophobicity, it has seemed to be an effective way to form a water repellent protective film by using a trialkylsilyl compound where the number of hydrocarbon groups bonded to silicon element is maximum. However, it was unexpectedly found that the water repellency is improved when a water repellent protective film is formed by using a dialkylsilyl compound where the number of hydrocarbon groups bonded to silicon element is two, as compared with the case of using a trialkylsilyl compound.

Effects of the Invention

In cleaning a wafer having an uneven pattern and containing silicon element at its surface, the use of a liquid chemical for forming a wafer pattern-protective film of the present invention contributes to the formation of a protective film that exhibits an excellent water repellency.

THE MODE FOR CARRYING OUT THE INVENTION

Figure 1:
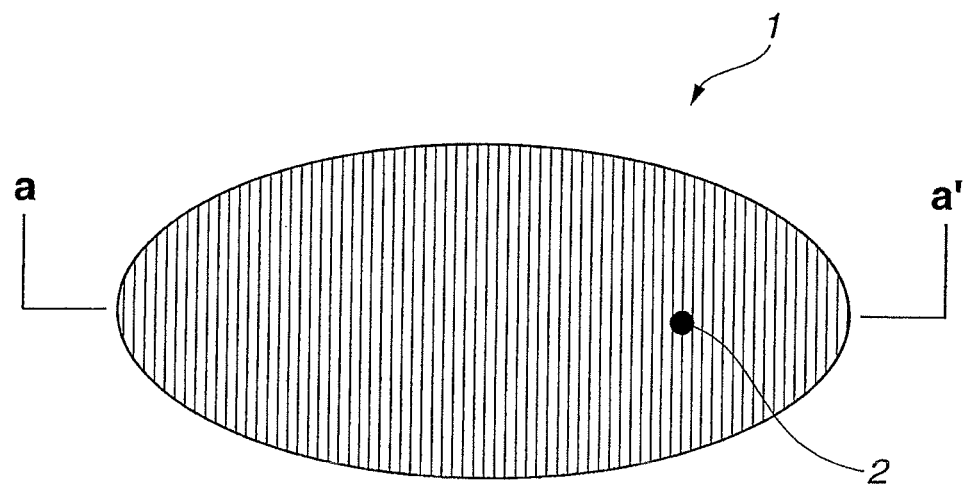
FIG. 1 A view showing a schematic perspective view of a wafer 1 of which surface is made into a surface having an uneven pattern 2.

The present invention will hereinafter be more specifically discussed.

[About Dialkylsilyl Compound]

Firstly, there will be discussed a dialkylsilyl compound represented by the general formula [1], the dialkylsilyl compound being a characteristic of a liquid chemical for forming a water repellent protective film which liquid chemical is provided by the present invention in order to prevent a pattern collapse (the liquid chemical will hereinafter be referred to as "a liquid chemical for forming a water repellent protective film" or "a liquid chemical for forming a protective film" or merely "a liquid chemical").

In a dialkylsilyl compound represented by the general formula [1], R mutually independently represents at least one group selected from monovalent organic groups having a $C_1$-$C_{18}$ hydrocarbon group and monovalent organic groups having a $C_1$-$C_8$ fluoroalkyl chain. X represents a group selected from halogen groups and monovalent organic groups of which element to be bonded to a silicon element is nitrogen. In the general formula [1], the monovalent organic groups (represented by X) of which element to be bonded to a silicon element is nitrogen may contain not only hydrogen element, carbon element, nitrogen element and oxygen element but also silicon element, sulfur element, halogen element and the like.

Of these, as a halogen group represented by X, it is possible to cite a fluorine group, a chlorine group, an iodine group and a bromine group. For example, in the case where X is a chlorine group, it is possible to cite $(CH_3)_2(H)Si—Cl$, $C_2H_5(CH_3)(H)Si—Cl$, $(C_2H_5)_2(H)Si—Cl$, $C_3H_7(CH_3)(H)Si—Cl$, $(C_3H_7)_2(H)Si—Cl$, $C_4H_9(CH_3)(H)Si—Cl$, $(C_4H_9)_2(H)Si—Cl$, $C_5H_{11}(CH_3)(H)Si—Cl$, $(C_5H_{11})_2(H)Si—Cl$, $C_6H_{13}(CH_3)(H)Si—Cl$, $(C_6H_{13})_2(H)Si—Cl$, $C_7H_{15}(CH_3)(H)Si—Cl$, $(C_7H_{15})_2(H)Si—Cl$, $C_8H_{17}(CH_3)(H)Si—Cl$, $(C_8H_{17})_2(H)Si—Cl$, $C_9H_{19}(CH_3)(H)Si—Cl$, $(C_9H_{19})_2(H)Si—Cl$, $C_{10}H_{21}(CH_3)(H)Si—Cl$, $(C_{10}H_{21})_2(H)Si—Cl$, $C_{11}H_{23}(CH_3)(H)Si—Cl$, $(C_{11}H_{23})_2(H)Si—Cl$, $C_{12}H_{25}(CH_3)(H)Si—Cl$, $(C_{12}H_{25})_2(H)Si—Cl$, $C_{13}H_{27}(CH_3)(H)Si—Cl$, $(C_{13}H_{27})_2(H)Si—Cl$, $C_{14}H_{29}(CH_3)(H)Si—Cl$, $(C_{14}H_{29})_2(H)Si—Cl$, $C_{15}H_{31}(CH_3)(H)Si—Cl$, $(C_{15}H_{31})_2(H)Si—Cl$, $C_{16}H_{33}(CH_3)(H)Si—Cl$, $(C_{16}H_{33})_2(H)Si—Cl$, $C_{17}H_{35}(CH_3)(H)Si—Cl$, $(C_{17}H_{35})_2(H)Si—Cl$, $C_{18}H_{37}(CH_3)(H)Si—Cl$, $(C_{18}H_{37})_2(H)Si—Cl$, $CF_3C_2H_4(CH_3)(H)Si—Cl$, $C_2F_5C_2H_4(CH_3)(H)Si—Cl$, $C_3F_7C_2H_4(CH_3)(H)Si—Cl$, $C_4F_9C_2H_4(CH_3)(H)Si—Cl$, $C_5F_{11}C_2H_4(CH_3)(H)Si—Cl$, $C_6F_{13}C_2H_4(CH_3)(H)Si—Cl$, $C_7F_{15}C_2H_4(CH_3)(H)Si—Cl$, $C_8F_{17}C_2H_4(CH_3)(H)Si—Cl$ and the like.

Additionally, as a monovalent organic group (represented by X in the general formula [1]) of which element to be bonded to a silicon element is nitrogen, it is possible to cite isocyanate group, amino group, dialkylamino group, azide group, acetamide group, imidazole group, $—NH—Si(H)R_2$ group (R is the same as the general formula [1]) and the like. For example, in the case where X is a $—NH—Si(H)R_2$ group, it is possible to cite $(CH_3)_2(H)Si—NH—Si(H)(CH_3)_2$, $C_2H_5(CH_3)(H)Si—NH—Si(H)(CH_3)C_2H_5$, $(C_2H_5)_2(H)Si—NH—Si(H)(C_2H_5)_2$, $C_3H_7(CH_3)(H)Si—NH—Si(H)(CH_3)C_3H_7$, $(C_3H_7)_2(H)Si—NH—Si(H)(C_3H_7)_2$, $C_4H_9(CH_3)(H)Si—NH—Si(H)(CH_3)C_4H_9$, $(C_4H_9)_2(H)Si—NH—Si(H)(C_4H_9)_2$, $C_5H_{11}(CH_3)(H)Si—NH—Si(H)(CH_3)C_5H_{11}$, $(C_5H_{11})_2(H)Si—NH—Si(H)(C_5H_{11})_2$, $C_6H_{13}(CH_3)(H)Si—NH—Si(H)(CH_3)C_6H_{13}$, $(C_6H_{13})_2(H)Si—NH—Si(H)(C_6H_{13})_2$, $C_7H_{15}(CH_3)(H)Si—NH—Si(H)(CH_3)C_7H_{15}$, $(C_7H_{15})_2(H)Si—NH—Si(H)(C_7H_{15})_2$, $C_8H_{17}(CH_3)(H)Si—NH—Si(H)(CH_3)C_8H_{17}$, $(C_8H_{17})_2(H)Si—NH—Si(H)(C_8H_{17})_2$, $C_9H_{19}(CH_3)(H)Si—NH—Si(H)(CH_3)C_9H_{19}$, $(C_9H_{19})_2(H)Si—NH—Si(H)(C_9H_{19})_2$, $C_{10}H_{21}(CH_3)(H)Si—NH—Si(H)(CH_3)C_{10}H_{21}$, $(C_{10}H_{21})_2(H)Si—NH—Si(H)(C_{10}H_{21})_2$, $C_{11}H_{23}(CH_3)(H)Si—NH—Si(H)(CH_3)C_{11}H_{23}$, $(C_{11}H_{23})_2(H)Si—NH—Si(H)(C_{11}H_{23})_2$, $C_{12}H_{25}(CH_3)(H)Si—NH—Si(H)(CH_3)C_{12}H_{25}$, $(C_{12}H_{25})_2(H)Si—NH—Si(H)(C_{12}H_{25})_2$, $C_{13}H_{27}(CH_3)(H)Si—NH—Si(H)(CH_3)C_{13}H_{27}$, $(C_{13}H_{27})_2(H)Si—NH—Si(H)(C_{13}H_{27})_2$, $C_{14}H_{29}(CH_3)(H)Si—NH—Si(H)(CH_3)C_{14}H_{29}$, $(C_{14}H_{29})_2(H)Si—NH—Si(H)(C_{14}H_{29})_2$, $C_{15}H_{31}(CH_3)(H)Si—NH—Si(H)(CH_3)C_{15}H_{31}$, $(C_{15}H_{31})_2(H)Si—NH—Si(H)(C_{15}H_{31})_2$, $C_{16}H_{33}(CH_3)(H)Si—NH—Si(H)(CH_3)C_{16}H_{33}$, $(C_{16}H_{33})_2(H)Si—NH—Si(H)(C_{16}H_{33})_2$, $C_{17}H_{35}(CH_3)(H)Si—NH—Si(H)(CH_3)C_{17}H_{35}$, $(C_{17}H_{35})_2(H)Si—NH—Si(H)(C_{17}H_{35})_2$, $C_{18}H_{37}(CH_3)(H)Si—NH—Si(H)(CH_3)C_{18}H_{37}$, $(C_{18}H_{37})_2(H)Si—NH—Si(H)(C_{18}H_{37})_2$, $CF_3C_2H_4(CH_3)(H)Si—NH—Si(H)(CH_3)C_2H_4CF_3$, $C_2F_5C_2H_4(CH_3)(H)Si—NH—Si(H)(CH_3)C_2H_4C_2F_5$, $C_3F_7C_2H_4(CH_3)(H)Si—NH—Si(H)(CH_3)C_2H_4C_3F_7$, $C_4F_9C_2H_4(CH_3)(H)Si—NH—Si(H)(CH_3)C_2H_4C_4F_9$, $C_5F_{11}C_2H_4(CH_3)(H)Si—NH—Si(H)(CH_3)C_2H_4C_5F_{11}$, $C_6F_{13}C_2H_4(CH_3)(H)Si—NH—Si(H)(CH_3)C_2H_4C_6F_{13}$, $C_7F_{15}C_2H_4(CH_3)(H)Si—NH—Si(H)(CH_3)C_2H_4C_7F_{15}$, $C_8F_{17}C_2H_4(CH_3)(H)Si—NH—Si(H)(CH_3)C_2H_4C_8F_{17}$ and the like.

Of dialkylsilyl compounds represented by the general formula [1], those having a carbon number of from 1 to 8 are preferable because the protective film can be formed within a shorter time.

Furthermore, it is preferable that a halogen group represented by X is a chlorine group. Moreover, a monovalent organic group (represented by X) of which element to be bonded to a silicon element is nitrogen is preferably $—NH—Si(H)R_2$ group.

Furthermore, in view of the availability, the most preferable compound among the silicon compounds represented by the general formula [1] is exemplified by dimethylchlorosilane and tetramethyldisilazane.

[About Liquid Chemical for Forming Protective Film]

Then, there will be discussed a liquid chemical for forming a water repellent protective film, the liquid chemical containing a dialkylsilyl compound represented by the general formula [1]. The liquid chemical of the present invention is required only to contain at least a water repellent protective film-forming agent.

For the liquid chemical, it is possible to use an organic solvent as a solvent. The organic solvent is required only to be such as to dissolve the protective film-forming agent. For example, hydrocarbons, esters, ethers, ketones, halogen element-containing solvents, sulfoxide-based solvents, polyalcohol derivatives having no hydroxyl group, nitrogen element-containing solvents and the like are preferably used.

Examples of hydrocarbons are toluene, benzene, xylene, hexane, heptane, octane and the like. Examples of esters are ethyl acetate, propyl acetate, butyl acetate, ethyl acetoacetate and the like. Examples of ethers are diethyl ether, dipropyl ether, dibutyl ether, tetrahydrofuran, dioxane and the like. Examples of ketones are acetone, acetylacetone, methyl ethyl ketone, methyl propyl ketone, methyl butyl ketone, cyclohexanone and the like. Examples of the halogen element-containing solvents are: perfluorocarbons such as perfluorooctane, perfluorononane, perfluorocyclopentane, perfluorocyclohexane, hexafluorobenzene and the like; hydrofluorocarbons such as 1,1,1,3,3-pentafluorobutane, octafluorocyclopentane, 2,3-dihydrodecafluoropentane, ZEORORA-H (produced by ZEON CORPORATION) and the like; hydrofluoroethers such as methyl perfluoroisobutyl ether, methyl perfluorobutyl ether, ethyl perfluorobutyl ether, ethyl perfluoroisobutyl ether, ASAHIKLIN AE-3000 (produced by Asahi Glass Co., Ltd.), Novec HFE-7100, Novec HFE-7200, Novec 7300, Novec 7600 (any of these are produced by 3M Limited) and the like; chlorocarbons such as tetrachloromethane and the like; hydrochlorocarbons such as chloroform and the like; chlorofluorocarbons such as dichlorodifluoromethane and the like; hydrochlorofluorocarbons such as 1,1-dichloro-2,2,3,3,3-pentafluoropropane, 1,3-dichloro-1,1,2,2,3-pentafluoropropane, 1-chloro-3,3,3-trifluoropropene, 1,2-dichloro-3,3,3-trifuoropropene and the like; perfluoroethers; perfluoropolyethers; and the like. Examples of the sulfoxide-based solvents are dimethyl sulfoxide and the like. Examples of the polyalcohol derivatives having no hydroxyl group are diethylene glycol monoethyl ether acetate, ethylene glycol monomethyl ether acetate, ethylene glycol monobutyl ether acetate, propylene glycol monomethyl ether acetate, propylene glycol monoethyl ether acetate, diethylene glycol dimethyl ether, diethylene glycol ethyl methyl ether, diethylene glycol diethyl ether, diethylene glycol monomethyl ether acetate, diethylene glycol diacetate, triethylene glycol dimethyl ether, triethylene glycol diethyl ether, dipropylene glycol dimethyl ether, ethylene glycol diacetate, ethylene glycol diethyl ether, ethylene glycol dimethyl ether and the like. Examples of the nitrogen element-containing solvents are formamide, N,N-dimethylformamide, N,N-dimethylacetamide, N-methyl-2-pyrrolidone, diethylamine, triethylamine, pyridine and the like. Of these solvents, hydrofluoroethers (such as Novec HFE-7100 and the like) and the polyalcohol derivatives having no hydroxyl group (such as propylene glycol monomethyl ether acetate and the like) are particularly preferably used.

Additionally, it is preferable to use a nonflammable solvent as the above-mentioned organic solvent since the liquid chemical for forming a protective film becomes nonflammable or increases in flash point. Most of the halogen element-containing solvents are nonflammable, so that such a halogen element-containing nonflammable solvent can be preferably used as a nonflammable organic solvent.

Additionally, the organic solvent accepts the abundance of a very smaller amount of water. However, when a large amount of water is contained in the solvent, the dialkylsilyl compound tends to cause hydrolysis due to the water content so as to sometimes be reduced in reactivity. It is therefore preferable that the solvent has a smaller water content. The water content is preferably not higher than 100 mass ppm, particularly preferably not higher than 50 mass ppm.

Moreover, the liquid chemical for forming a protective film, according to the present invention makes it possible to form a protective film having water-repellent ability, without containing acid or base as a catalyst. By the way, the phrase "without containing acid or base" concretely means that acid or base is not higher than 100 mass ppm relative to the total amount of the liquid chemical.

Furthermore, it is preferable that the content of the dialkylsilyl compound contained in the liquid chemical is 0.1 to 50 mass % relative to 100 mass % of the total amount of the liquid chemical, and more preferably 0.3 to 20 mass % relative to 100 mass % of the total amount of the liquid chemical. When the content of the alkylsilyl compound is lower than 0.1 mass %, the alkylsilyl compound should be reacted with a small amount of water content and the like included in the organic solvent to cause deactivation; therefore an ability to form a water repellent protective film is so poor as not to impart a sufficient water repellency to the wafer surface. Meanwhile, the case where the content of the alkylsilyl compound is higher than 50 mass % is not preferable from a fear that the dialkylsilyl compound remains on the wafer surface as an impurity and from the viewpoint of the cost.

[About Cleaning Method]

Then, a method for cleaning the wafer, according to the present invention will be discussed. In general, as a wafer to be cleaned by using the liquid chemical of the present invention, there is often used one that has been subjected to a pretreatment step where a surface of a wafer is made into a surface having an uneven pattern.

A method for the pretreatment step is not particularly limited as far as it is possible to form a wafer to have a patterned surface; however, in an usual method therefor, a resist is applied to a surface of a wafer and then the resist is exposed to light through a resist mask, followed by conducting an etching removal on the exposed resist or an unexposed resist thereby producing a resist having a desired uneven pattern. Additionally, the resist having an uneven pattern can be obtained also by pushing a mold having a pattern onto the resist. Then, etching is conducted on the wafer. At this time, the wafer surface corresponding to recessed portions of the resist pattern are etched selectively. Finally, the resist is stripped off thereby obtaining a wafer having an uneven pattern.

Incidentally, the above-mentioned wafer includes: silicon wafers; silicon wafers on which surface a film containing silicon element is formed, such as silicon oxide (hereinafter, sometimes referred to as $SiO_2$), silicon nitride (hereinafter, sometimes referred to as SiN) and the like; and wafers formed to contain silicon element such as silicon, silicon oxide, silicon nitride and the like at the surface of the uneven pattern, in the case where the uneven pattern is formed.

Additionally, also on wafers consisting of a plurality of components including at least one selected from silicon, silicon oxide and silicon nitride, it is possible to form the water repellent protective film on a surface of a portion where silicon element is present. The wafers consisting of a plurality of components are exemplified by: wafers on which surface at least one selected from silicon, silicon oxide and silicon nitride is formed; and wafers formed to contain at least one selected from silicon, silicon oxide, silicon nitride at least at surfaces of recessed portions of the uneven pattern, in the case where the uneven pattern is formed. Furthermore, wafers that do not contain silicon, such as sapphire wafers, various compound semiconductor wafers, plastic wafers and the like, and formed with various films containing silicon thereon are also acceptable.

The present invention is a method for cleaning a wafer having an uneven pattern at its surface, the wafer containing silicon element at least at surfaces of recessed portions of the uneven pattern, and involves:

a cleaning step with a water-based cleaning liquid, in which a surface of the wafer is cleaned with a water-based cleaning liquid;

a water repellent protective film-forming step, in which a liquid chemical for forming a protective film is retained at least in the recessed portions of the wafer so as to form a water repellent protective film on the surfaces of the recessed portions;

a liquid removal step for removing a liquid from the surface of the wafer; and a water repellent protective film-removing step for removing the water repellent protective film from the surfaces of the recessed portions.

Examples of the water-based cleaning liquid include liquids containing water as the primary component (for example, liquids having a 50 mass % or more water content), such as water and a mixture obtained by mixing at least one kind of an organic solvent, acid and alkali into water.

Figure 2:
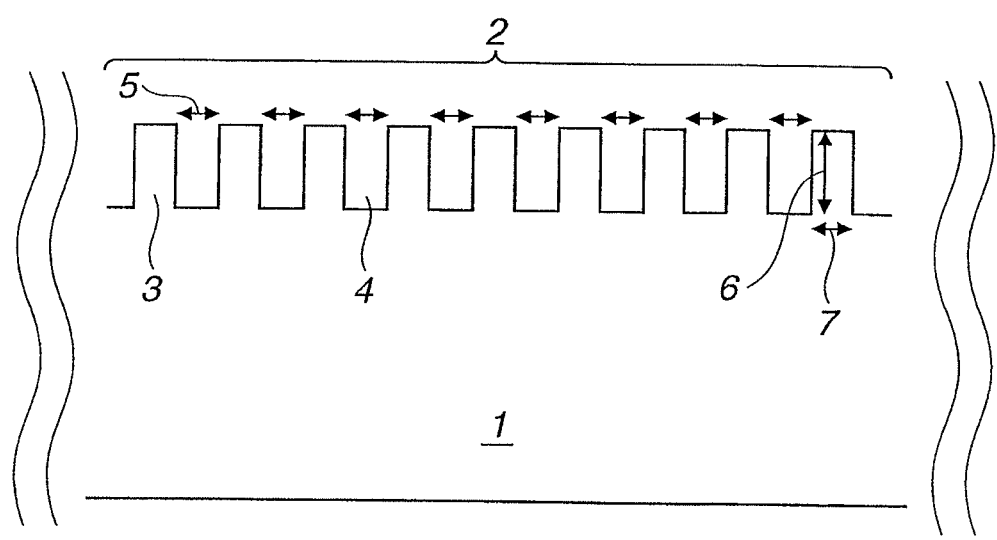
FIG. 2 A view showing a part of a-a' cross section of FIG. 1.

In the cleaning step with a water-based cleaning liquid, a resist is removed and particles on the surface of the wafer are removed, and then a water-based cleaning liquid is removed by drying or the like. If the recessed portions have a small width and projected portions have a large aspect ratio at this time, the pattern collapse is to easily occur. The uneven pattern is defined as shown in FIG. 1 and FIG. 2. FIG. 1 is a view showing a schematic perspective view of a wafer 1 of which surface is made into a surface having an uneven pattern 2. FIG. 2 is a view showing a part of a-a' cross section of FIG. 1. A width 5 of recessed portions is defined by an interval between adjacent projected portions 3, as shown in FIG. 2. The aspect ratio of projected portions is expressed by dividing a height 6 of the projected portions by a width 7 of the projected portions. The pattern collapse in the cleaning step is to easily occur when the recessed portions have a width of not more than 70 nm, particularly not more than 45 nm and when the aspect ratio is not less than 4, particularly not less than 6.

In the method for cleaning a wafer according to the present invention, in order to efficiently perform cleaning without causing the pattern collapse, it is preferable that the cleaning step with a water-based cleaning liquid and the water repellent protective film-forming step are carried out under a condition where a liquid is invariably retained at least in the recessed portions of the wafer. Also in the case of substituting the liquid chemical for forming a water repellent protective film retained in the recessed portions of the wafer with another liquid after the water repellent protective film-forming step, it is preferable to carry out it under a condition where a liquid is invariably retained at least in the recessed portions of the wafer, similarly to the above. In the present invention, it is essential only that the water-based cleaning liquid, the liquid chemical or another liquid is retained at least on the surfaces of the recessed portions of the uneven pattern of the wafer; therefore, a cleaning style for a wafer is not particularly limited. Examples of the cleaning style for a wafer are: a sheet cleaning style represented by spin cleaning where the wafer is cleaned one by one in such a manner as to dispose the wafer generally horizontally and rotate it while supplying a liquid to the vicinity of the center of the rotation; and a batch style where a plurality of the wafer are cleaned in a cleaning bath by being immersed therein. Incidentally, the form of the water-based cleaning liquid, the liquid chemical or the other liquid at the time of supplying the water-based cleaning liquid, the liquid chemical or the other liquid at least to the surfaces of the recessed portions of the uneven pattern of the wafer is not particularly limited as far as it becomes the form of liquid at time of being retained in the recessed portions, and may be liquid, vapor or the like, for instance.

Next, the water repellent protective film-forming step will be discussed. A shift from the cleaning step with a water-based cleaning liquid to the water repellent protective film-forming step is achieved by substituting the water-based cleaning liquid having been retained in the recessed portions of the uneven pattern of the wafer during the cleaning step with a water-based cleaning liquid with the liquid chemical for forming a water repellent protective film. The substitution of the water-based cleaning liquid with the liquid chemical for forming a water repellent protective film may be a direct substitution, or may be a substitution where the water-based cleaning liquid is substituted with a different cleaning liquid (A) (hereinafter, sometimes referred to merely as "a cleaning liquid (A)") one or more time and thereafter substituted with the liquid chemical for forming a water repellent protective film. Preferable examples of the cleaning liquid (A) include water, an organic solvent, a mixture of water and an organic solvent, a mixture of these and at least one kind of acid, alkali and a surfactant, and the like. Additionally, examples of the organic solvents, which is one of the preferable examples of the cleaning liquid (A), include hydrocarbons, esters, ethers, ketones, halogen element-containing solvents, sulfoxide-based solvents, alcohols, polyalcohol derivatives, nitrogen element-containing solvents and the like.

Figure 3:
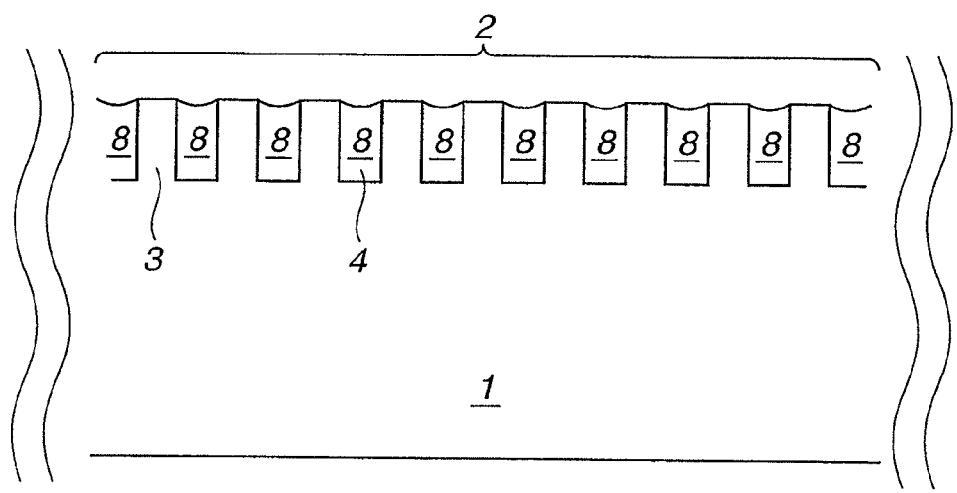
FIG. 3 A schematic view showing a condition where a liquid chemical 8 for forming a water repellent protective film is retained in recessed portions 4.

Formation of the water repellent protective film during the water repellent protective film-forming step is carried out by retaining the liquid chemical for forming a protective film at least in the recessed portions of the uneven pattern of the wafer. FIG. 3 is a schematic view showing a condition where the liquid chemical 8 for forming a protective film is retained in the recessed portions 4. The wafer of the schematic view of FIG. 3 shows a part of an a-a' cross section in FIG. 1. At the time of the water repellent protective film-forming step, the liquid chemical for forming a protective film is provided onto the wafer 1 in which the uneven pattern 2 is formed. At this time, the liquid chemical for forming a water repellent protective film is brought into a condition retained at least in the recessed portions 4 as shown in FIG. 3, thereby imparting water repellency to the surfaces of the recessed portions 4. Incidentally, the protective film of the present invention is not necessarily formed continuously, and not necessarily formed evenly; however, it is preferable to form it continuously and evenly in order to provide a more excellent water repellency.

When the temperature of the liquid chemical is increased in the protective film-forming step, the protective film can be formed easily in a shorter time. However, there is a fear that the liquid chemical for forming a water repellent protective film loses stability due to its boiling, vaporization or the like, so that the liquid chemical is preferably retained at 10 to 160° C., particularly preferably at 15 to 120° C.

Figure 4:
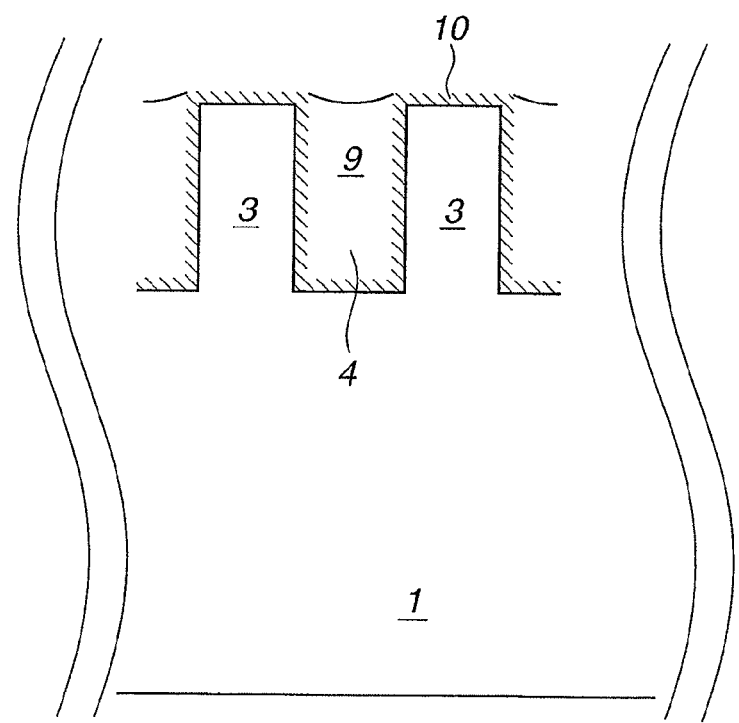
FIG. 4 A view showing a schematic view of a condition where a liquid 9 is retained in the recessed portions 4 on which a water repellent protective film 10 is formed.

A schematic view of a condition where a liquid 9 is retained in the recessed portions 4 provided with water repellency by a water repellent protective film-forming agent is shown in FIG. 4. The wafer as shown in the schematic view of FIG. 4 shows a part of an a-a' cross section of FIG. 1. On the surfaces of the recessed portions 4, a water repellent protective film 10 is formed by a water repellent protective film-forming agent. The liquid 9 retained in the recessed portions 4 at this time may be the liquid chemical, or a liquid (a cleaning liquid (B)) after substituting the liquid chemical with a liquid which is different from the liquid chemical (hereinafter, sometimes referred to merely as "a cleaning liquid (B)"), or a liquid on the way to substitution (i.e., a mixed liquid of the liquid chemical and the cleaning liquid). The water repellent protective film 10 is retained on the surface of the wafer even when the liquid 9 is removed from the recessed portions 4.

Preferable examples of the cleaning liquid (B) include water, an organic solvent, a mixture of water and an organic solvent, a mixture of these and at least one kind of acid, alkali and a surfactant, and the like. Additionally, examples of the organic solvents, which is one of the preferable examples of the cleaning liquid (B), include hydrocarbons, esters, ethers, ketones, halogen element-containing solvents, sulfoxide-based solvents, alcohols, polyalcohol derivatives, nitrogen element-containing solvents and the like.

When a liquid is retained in the recessed portions of the wafer having an uneven pattern, a capillary force is to act on the recessed portions. The magnitude of the capillary force is an absolute value "P" obtained by the equation as represented below.

$$P = 2 \times \gamma \times \cos\theta / S$$

(In the equation, γ represents the surface tension of a liquid retained in the recessed portions, θ represents the contact angle of the liquid retained in the recessed portions to the surfaces of the recessed portions, and S represents the width of the recessed portions.)

If a water repellent protective film exists on the surfaces of the recessed portions as shown by the recessed portions 4 of FIG. 4, θ is to increase while decreasing the absolute value "P". From the viewpoint of suppressing the pattern collapse, a smaller absolute value "P" is more preferable, and it is ideal to put the capillary force close to 0.0 MN/m² as much as possible by adjusting the contact angle of the liquid to be removed to around 90°. When the protective film 10 is formed on the surfaces of the recessed portions as shown in FIG. 4, a contact angle of from 60 to 120° is preferable on the assumption that water is retained on the surfaces, because the pattern collapse becomes difficult to occur. The closer to 90° the contact angle is, the smaller the capillary force acting on the recessed portions becomes, so that the pattern collapse is made further difficult to occur. It is therefore preferable that the contact angle is from 70 to 110°.

Next, the liquid removal step will be discussed. Incidentally, the liquid retained in the recessed portions is the liquid chemical, the cleaning liquid (B) or the mixed liquid of the liquid chemical and the cleaning liquid (B). As a method for removing the liquid, it is preferable to conduct a conventionally known drying method such as natural drying, air drying, $N_2$ gas drying, spin drying, IPA (2-propanol) steam drying, Marangoni drying, heating drying, warm air drying, vacuum drying and the like. In order to remove the liquid with efficiency, the retained liquid may be drained and then the remaining liquid may be subjected to drying.

Finally, there will be discussed the water repellent protective film-removing step. At the time of removing the water repellent protective film, it is effective to cleave C—C bond and C—F bond in the protective film. A method therefor is not particularly limited so long as it is possible to cleave the above-mentioned bonds, and exemplified by: irradiating the wafer surface with light; heating the wafer; exposing the wafer to ozone; irradiating the wafer surface with plasma; subjecting the wafer surface to corona discharge; and the like.

In the case of removing the protective film by light irradiation, it is preferable to conduct an irradiation with ultraviolet rays having a wavelength of shorter than 340 nm and 240 nm (corresponding to bond energies of C—C bond and C—F bond, i.e., 83 kcal/mol and 116 kcal/mol, respectively). As the light source therefor, there is used a metal halide lamp, a low-pressure mercury lamp, a high-pressure mercury lamp, an excimer lamp, a carbon arc or the like.

Additionally, in the case of removing the protective film by light irradiation, it is particularly preferable to generate ozone in parallel with decomposing the components of the protective film by ultraviolet rays and then to induce oxidation-volatilization of the components of the protective film by the ozone, since a treatment time is saved thereby. As the light source therefor, the low-pressure mercury lamp, the excimer lamp or the like may be used. Moreover, the wafer may be heated while being subjected to light irradiation.

In the case of heating the wafer, it is preferable to conduct heating of the wafer at 400 to 700° C., preferably at 500 to 700° C. The heating time is preferably kept for 1 to 60 minutes, and more preferably for 10 to 30 minutes. Additionally, this step may be conducted in combination with ozone exposure, plasma irradiation, corona discharge or the like. Furthermore, the light irradiation may be conducted while heating the wafer.

A method for removing the protective film by heating is exemplified by a method of bringing a wafer into contact with a heat source, a method of setting a wafer aside in a heated atmosphere such as a heat treat furnace and the like, and the like. Incidentally, the method of setting a wafer aside in a heated atmosphere can easily and evenly impart energy for removing the protective film to the wafer surface even in the case of treating the plural sheets of wafers, and therefore serves as an industrially advantageous method with simple operations, a short treatment time and a high treatment capacity.

In the case of exposing the wafer to ozone, it is possible to expose the wafer surface to ozone generated by ultraviolet irradiation using the low-pressure mercury lamp, low-temperature discharge using high voltages or the like. The wafer may be irradiated with light or heated while being exposed to ozone.

By combining light irradiation, heating, ozone exposure, plasma irradiation, corona discharge and the like, it becomes possible to efficiently remove the protective film formed on the wafer surface.

EXAMPLES

A technique of making a surface of a wafer into a surface having an uneven pattern and a technique of substituting a cleaning liquid retained at least in recessed portions of the uneven pattern with another cleaning liquid have been variously studied as discussed in other literatures and the like, and have already been established. Accordingly, in Examples of the present invention, there were mainly performed evaluations concerning a liquid chemical for forming a protective film. Additionally, as apparent from the equation represented by "$P=2\times\gamma\times\cos\theta/S$" (In the equation, $\gamma$ represents the surface tension of a liquid retained in the recessed portions, $\theta$ represents the contact angle of the liquid retained in the recessed portions to the surfaces of the recessed portions, and S represents the width of the recessed portions) discussed in the section "BACKGROUND OF THE INVENTION" and the like, a pattern collapse greatly depends on the contact angle of a cleaning liquid to the surface of the wafer, i.e. the contact angle of a liquid drop and on the surface tension of the cleaning liquid. In the case of a cleaning liquid retained in recessed portions 4 of an uneven pattern 2, the contact angle of a liquid drop and the capillary force acting on the recessed portions (which force can be regarded as being equal to the pattern collapse) are in correlation with each other, so that it is possible to derive the capillary force from the equation and the evaluations made on the contact angle of the liquid drop to a protective film 10.

An evaluation of the contact angle of waterdrop is conducted by dropping several microliters of waterdrop on a surface of a sample (a substrate) and then by measuring an angle formed between the waterdrop and the substrate surface, as discussed in JIS R 3257 (Testing method of wettability of glass substrate surface). However, in the case of a wafer having a pattern, the contact angle is enormously large. This is because Wenzel's effect or Cassie's effect is caused so that an apparent contact angle of the waterdrop is increased under the influence of a surface shape (roughness) of the substrate upon the contact angle. Hence, in the case of a wafer having an unevenly patterned surface, it is not possible to exactly evaluate the contact angle of the protective film 10 itself, the protective film 10 being formed on the unevenly patterned surface.

In view of the above, in Examples of the present invention, the liquid chemical is supplied onto a wafer having a smooth surface to form a protective film on the surface of the wafer, the protective film being regarded as a protective film 10 formed on the surface of a wafer 1 having at its surface an uneven pattern 2, thereby performing various evaluations. In Examples of the present invention, there was used "a silicon wafer with a $SiO_2$ film" (shown in Table as $SiO_2$) which is a silicon wafer formed having a silicon oxide layer on its surface.

Details will be discussed below. Hereinafter, there will be discussed: a method for evaluating a wafer to which a liquid chemical for forming a protective film is supplied; preparation of the liquid chemical for forming a protective film; and results of evaluation made after supplying the liquid chemical for forming a protective film to the wafer.

[Method for Evaluating Wafer to which Liquid Chemical for Forming Protective Film is Provided]

As a method for evaluating a wafer to which a liquid chemical for forming a protective film is provided, the following evaluations (1) to (3) were performed.

(1) Evaluation of Contact Angle of Protective Film Formed on Wafer Surface

About 2 µl of pure water was dropped on a surface of a wafer on which a protective film was formed, followed by measuring an angle (contact angle) formed between the waterdrop and the wafer surface by using a contact angle meter (produced by Kyowa Interface Science Co., Ltd.:

CA-X Model). The closer to 90° the contact angle is (or the closer to 0.0 MN/m² as much as possible the capillary force is), the more effective it is; hence a sample where a contact angle to the protective film was within a range of from 60 to 120° was classified as acceptable.

(2) Removability of Protective Film

A sample was irradiated with UV rays from a low-pressure mercury lamp for 1 minute under the following conditions, upon which the removability of the protective film exhibited in the water repellent protective film-removing step was evaluated. A sample on which waterdrop had a contact angle of not larger than 10° after the irradiation was classified as acceptable one (indicated in Table with A).

Lamp: PL2003N-10 produced by SEN LIGHTS CORPORATION

Illuminance: 15 mW/cm² (the distance from the light source to the sample was 10 mm)

(3) Evaluation of Surface Smoothness of Wafer after Removing Protective Film

The surface was observed by atomic force microscope (produced by Seiko Instruments Inc.: SPI3700, 2.5 micrometer square scan) thereby obtaining the centerline average surface roughness Ra (nm). Incidentally, "Ra" is a three-dimensionally enlarged one obtained by applying the centerline average roughness defined by JIS B 0601 to a measured surface and is calculated as "an average value of absolute values of difference from standard surface to designated surface" from the following equation. If the Ra value of the wafer surface after the protective film was removed therefrom was not larger than 1 nm, the wafer surface was regarded as not being eroded by the cleaning and regarded as not leaving residues of the protective film thereon, and therefore classified as an acceptable one (indicated in Table with A).

$$Ra = \frac{1}{S_0} \int_{Y_T}^{Y_B} \int_{X_L}^{X_R} |F(X, Y) - Z_0| dX dY$$

wherein $X_L$ and $X_R$, and $Y_B$ and $Y_T$ represent a measuring range in the X coordinate and the Y coordinate, respectively. $S_0$ represents an area obtained on the assumption that the measured surface is ideally flat, and is a value obtained by $(X_R-X_L) \times (Y_B-Y_T)$. Additionally, $F(X,Y)$ represents the height at a measured point $(X,Y)$. $Z_0$ represents the average height within the measured surface.

Example 1

(1) Preparation of Liquid Chemical for Forming Protective Film

A mixture of: 3 g of tetramethyldisilazane [(CH₃)₂(H)Si—NH—Si(H)(CH₃)₂] that serves as a dialkylsilyl compound; and 97 g of propylene glycol monomethyl ether acetate (PGMEA) that serves as an organic solvent was prepared, followed by stirring for about 5 minutes, thereby obtaining a liquid chemical for forming a protective film in which a concentration of a protective film-forming agent (hereinafter referred to as "a protective film forming agent concentration") was 3 mass % relative to the total amount of the liquid chemical for forming a protective film.

(2) Cleaning of Wafer

A silicon wafer having a smooth SiO₂ film (a silicon wafer on which surface a thermal oxide film of 1 μm thickness was formed) was immersed in 1 mass % hydrogen fluoride aqueous solution for 2 minutes, and immersed in pure water for 1 minute, and then immersed in 2-propanol for 1 minute.

(3) Surface Treatment of Surface of Wafer, Using Liquid Chemical for Forming Protective Film The silicon wafer was immersed in the liquid chemical for forming a protective film (the liquid chemical having been prepared as discussed in the above "(1) Preparation of Liquid Chemical for forming Protective Film" section) at 20° C. for 1 minute. Subsequently, the silicon wafer was immersed in 2-propanol for 1 minute and then immersed in pure water for 1 minute. Finally, the silicon wafer was taken out of the pure water, followed by spraying air thereon to remove the pure water from the surface.

As a result of evaluating the thus obtained wafer in a manner discussed in the above [Method for Evaluating Wafer to which Liquid Chemical for forming Protective Film is provided] section, a wafer having an initial contact angle of smaller than 10° before the surface treatment had a contact angle of 66° after the surface treatment as shown in Table, with which it was confirmed that a water repellency-imparting effect was exhibited. Moreover, the contact angle of the wafer after UV irradiation was smaller than 10°, with which it was confirmed that removal of the protective film was achieved. Furthermore, a Ra value of the wafer after UV irradiation was smaller than 0.5 nm, so that it was confirmed that the wafer was not eroded at the time of cleaning and that residues of the protective film did not remain after UV irradiation.

Examples 2 to 6

Upon modifying the conditions employed in Example 1 (i.e., the protective film-forming agent, the protective film forming agent concentration and the organic solvent), a surface treatment was conducted on wafers, followed by evaluation of these. Results are shown in Table 1. Incidentally, in Table 1, "HFE-7100" means hydrofluoroether (Novec HFE-7100 produced by 3M Limited), and (CH₃)₂(H)Si—Cl means dimethylchlorosilane. "HFE-7100/PGMEA" means a mixed solvent in which HFE-7100:PGMEA is 95:5 in mass ratio.

Comparative Example 1

The procedure of Example 3 was repeated with the exception that hexamethyldisilazane [(CH₃)₃Si—NH—Si(CH₃)₃] was used as a protective film forming agent. Results of the evaluation are as shown in Table. The contact angle obtained after the surface treatment was 30° and therefore a water repellency-imparting effect was not enough.

Comparative Example 2

The procedure of Example 6 was repeated with the exception that trimethylchlorosilane [(CH₃)₃Si—Cl] was used as a protective film forming agent. Results of the evaluation are as shown in Table. The contact angle obtained after the surface treatment was 50° and therefore a water repellency-imparting effect was not enough.

Example 3 and Comparative Example 1 were conducted under the same conditions with the exception that the used silicon compound was a dialkylsilyl compound (Example 3) or a trimethylsilyl compound (Comparative Example 1). However, Comparative Example 1 resulted in the contact angle of 30° after the surface treatment to exhibit an unsatisfactory water repellency-imparting effect, while Example 3 resulted in the contact angle of 81° after the surface treatment to exhibit an extremely excellent water repellency-imparting effect. This means that a dimethylsilyl compound lower in number of methyl groups (that behave as hydrophobic groups) is superior in respect of the water repellency-imparting effect. A result between Example 6 and Comparative Example 2 is similar to the above, in which the water repellency-imparting effect was not sufficiently obtained by trimethylchlorosilane while dimethylchlorosilane had a good water repellency-imparting effect.

TABLE 1

| | Liquid Chemical for Forming Water Repellent Protective Film Starting Materials | | | Evaluation Results | | | |
|---|---|---|---|---|---|---|---|
| | Protective Film Forming Agent | Protective Film Forming Agent Concentration [mass %] | Organic Solvent | Initial Contact Angle [°] | Contact Angle after Surface Treatment [°] | Removability of Protective Film (Contact Angle [°]) | Surface Smoothness (Ra [nm]) |
| Example 1 | $(CH_3)_2(H)Si-NH-Si(H)(CH_3)_2$ | 3 | PGMEA | <10 | 66 | A(<10) | A(<0.5) |
| Example 2 | $(CH_3)_2(H)Si-NH-Si(H)(CH_3)_2$ | 5 | PGMEA | <10 | 71 | A(<10) | A(<0.5) |
| Example 3 | $(CH_3)_2(H)Si-NH-Si(H)(CH_3)_2$ | 10 | PGMEA | <10 | 81 | A(<10) | A(<0.5) |
| Example 4 | $(CH_3)_2(H)Si-NH-Si(H)(CH_3)_2$ | 3 | HFE-7100 | <10 | 91 | A(<10) | A(<0.5) |
| Example 5 | $(CH_3)_2(H)Si-NH-Si(H)(CH_3)_2$ | 3 | HFE-7100/PGMEA | <10 | 88 | A(<10) | A(<0.5) |
| Example 6 | $(CH_3)_2(H)Si-Cl$ | 10 | PGMEA | <10 | 70 | A(<10) | A(<0.5) |
| Comparative Example 1 | $(CH_3)_3Si-NH-Si(CH_3)_3$ | 10 | PGMEA | <10 | 30 | — | — |
| Comparative Example 2 | $(CH_3)_3Si-Cl$ | 10 | PGMEA | <10 | 50 | — | — |

INDUSTRIAL APPLICABILITY

A liquid chemical for forming protective film, and a method of cleaning wafers by using the liquid chemical according to the present invention contribute to improvements of production efficiency and production yield of devices in the field of integrated circuits of electronic industry.

EXPLANATION OF REFERENCE NUMERALS

1 Wafer
2 Uneven pattern on a wafer surface
3 Projected portions of the pattern
4 Recessed portions of the pattern
5 Width of the recessed portions
6 Height of the projected portions
7 Width of the projected portions
8 Liquid chemical for forming a water repellent protective film, retained in the recessed portions 4
9 Liquid retained in the recessed portions 4
10 Water repellent protective film

The invention claimed is:

1. A liquid chemical for forming a water repellent protective film, the liquid chemical being able to form a protective film on a wafer that has at its surface an uneven pattern and contains silicon element at least at surfaces of recessed portions of the uneven pattern, the protective film being formed at least on the surfaces of the recessed portions of the uneven pattern at the time of cleaning the wafer, the liquid chemical comprising:
   a dialkylsilyl compound represented by the following general formula [1], $$R_2(H)SiX \quad [1],$$

and
   an organic solvent;
   wherein the liquid chemical does not contain an acid and a base,
   wherein R mutually independently represents at least one group selected from monovalent organic groups having a $C_1$-$C_{18}$ hydrocarbon group and monovalent organic groups having a $C_1$-$C_8$ fluoroalkyl chain, and
   wherein X represents a group selected from halogen groups and monovalent organic groups of which element to be bonded to a silicon element is nitrogen.

2. A liquid chemical for forming a water repellent protective film as claimed in claim 1, wherein X is a halogen group.

3. A liquid chemical for forming a water repellent protective film as claimed in claim 1, wherein X is a monovalent organic group of which element to be bonded to a silicon element is nitrogen.

4. A liquid chemical for forming a water repellent protective film as claimed in claim 1, wherein the dialkylsilyl compound represented by the general formula [1] is represented by the following general formula [2]

$$R_2(H)Si-NH-Si(H)R_2 \quad [2]$$

wherein R is identical to that in the general formula [1].

5. A method for cleaning a wafer that has an uneven pattern at its surface and contains silicon element at least at surfaces of recessed portions of the uneven pattern, comprising:
   (1) a cleaning step with a water-based cleaning liquid, in which a surface of the wafer is cleaned with a water-based cleaning liquid;
   (2) a water repellent protective film-forming step, in which a liquid chemical for forming a water repellent protective film is retained at least in the recessed portions of the wafer so as to form a water repellent protective film on the surfaces of the recessed portions;
   (3) a liquid removal step for removing a liquid from the surface of the wafer; and
   (4) a water repellent protective film-removing step for removing the water repellent protective film from the surfaces of the recessed portions,
wherein the liquid chemical for forming a water repellent protective film as claimed in claim 1, is used in the water repellent protective film-forming step.

* * * * *